(12) United States Patent
Clifford et al.

(10) Patent No.: US 8,870,868 B2
(45) Date of Patent: Oct. 28, 2014

(54) EXTERNAL ANKLE DISTRACTION AND LOAD BYPASSING SYSTEM AND METHOD

(71) Applicant: Moximed, Inc., Hayward, CA (US)

(72) Inventors: Anton G. Clifford, Mountain View, CA (US); Imraan Aziz, Oakland, CA (US); Thomas King, Redwood City, CA (US); Michael Strasser, San Francisco, CA (US)

(73) Assignee: Moximed, Inc., Hayward, CA (US)

( * ) Notice: Subject to any disclaimer, the term of this patent is extended or adjusted under 35 U.S.C. 154(b) by 0 days.

(21) Appl. No.: 13/691,490

(22) Filed: Nov. 30, 2012

(65) Prior Publication Data

US 2013/0158550 A1    Jun. 20, 2013

Related U.S. Application Data

(60) Provisional application No. 61/566,178, filed on Dec. 2, 2011.

(51) Int. Cl.
| | |
|---|---|
| *A61B 17/66* | (2006.01) |
| *A61B 17/84* | (2006.01) |
| *A61B 17/64* | (2006.01) |
| *A61B 17/17* | (2006.01) |
| *A61B 17/16* | (2006.01) |
| *A61B 17/56* | (2006.01) |

(52) U.S. Cl.
CPC ............. *A61B 17/66* (2013.01); *A61B 17/1703* (2013.01); *A61B 17/1739* (2013.01); *A61B 17/1682* (2013.01); *A61B 2017/564* (2013.01); *A61B 17/848* (2013.01); *A61B 2017/1775* (2013.01); *A61B 17/1728* (2013.01); *A61B 17/6425* (2013.01)

USPC .......................................................... 606/55

(58) Field of Classification Search
USPC ............. 606/54, 55; 623/23.39–23.41, 47–56
See application file for complete search history.

(56) References Cited

U.S. PATENT DOCUMENTS

| | | | |
|---|---|---|---|
| 6,409,695 B1 * | 6/2002 | Connelly | ......................... 602/27 |
| 6,436,149 B1 | 8/2002 | Rincoe | |
| 6,461,358 B1 * | 10/2002 | Faccioli et al. | ................. 606/57 |
| 2009/0318976 A1 | 12/2009 | Gabriel et al. | |

FOREIGN PATENT DOCUMENTS

| | | |
|---|---|---|
| JP | 2004147867 | 5/2004 |
| JP | 2007089633 | 4/2007 |
| WO | WO2006053283 | 5/2006 |

OTHER PUBLICATIONS

International Preliminary Report on Patentability for PCT Patent App. No. PCT/US2012/067446 (Jun. 12, 2014).

* cited by examiner

*Primary Examiner* — Pedro Philogene
*Assistant Examiner* — David Comstock
(74) *Attorney, Agent, or Firm* — Cermak Nakajima & McGowan LLP; Adam J. Cermak

(57) ABSTRACT

Ankle distraction or load bypassing devices include a shoe or shoe insert that securely holds a patient's foot, and a cuff that securely holds the patient's lower leg. A load bypassing device can transmit force between the cuff and the shoe or shoe insert bypassing a portion of the load around the joint. A distraction force generating mechanism between the cuff and the shoe or shoe insert can distract the patient's ankle, while permitting the ankle to flex at a joint which joins together the cuff and the shoe.

41 Claims, 15 Drawing Sheets

EXTERNAL ANKLE DISTRACTION AND LOAD BYPASSING SYSTEM AND METHOD

BACKGROUND

1. Field of Endeavor

The present invention relates to devices, systems, and processes useful for distraction of a mammalian ankle or bypassing load around the ankle joint, and more specifically to the distraction or load bypassing for human ankles 2. Brief Description of the Related Art The present disclosure is directed toward apparatus and methods for treating joints and in particular, to treating ankle joints affected with osteoarthritis.

A joint is the location at which two or more bones make contact. Joints are constructed to allow movement and provide mechanical support, and are classified structurally and functionally. Structural classification is determined by how the bones connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. In fibrous/immovable joints, bones are connected by dense connective tissue, consisting mainly of collagen. The fibrous joints are further divided into three types:
  sutures which are found between bones of the skull;
  syndesmosis which are found between long bones of the body; and
  gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Cartilaginous joints include the artificial discs of the spine.

Synovial joints have a space between the articulating bones and surrounding cartilage for synovial fluid. This classification contains joints that are the most mobile of the three, and includes the hip, knee, ankle and shoulder.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Diarthrosis joints permit a variety of movements (e.g. flexion, adduction, pronation). Only synovial joints are diarthrodial and they can be divided into six classes according to their motion: 1. ball and socket—such as the shoulder or the hip; 2. hinge—such as the elbow and ankle; 3. pivot—such as the radius and ulna; 4. condyloidal (or ellipsoidal)—such as the wrist between radius and carps or knee; 5. saddle—such as the thumb joint; and 6. gliding—such as between the carpals.

Synovial joints (or diarthrosis or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

The main symptoms of osteoarthritis include chronic pain, causing loss of mobility and often stiffness. "Pain" is generally described as a sharp ache, or a burning sensation in the associated muscles and tendons. OA can cause a crackling noise (called "crepitus") when the affected joint is moved or touched, and patients may experience muscle spasm and contractions in the tendons. Occasionally, the joints may also be filled with fluid. Humid weather increases the pain in many patients.

OA affects the hand, feet, spine, and the large weight-bearing joints, such as the hips, knees and ankles, although in theory, any joint in the body can be affected. OA may begin or progress if excess stress or weight is placed on the knee joint. Several conditions can lead to excess stress or weight on the joint, including anatomy, injury, or obesity. When too much stress is placed on the knee as OA progresses, the affected joints appear larger, are stiff and painful, and usually feel worse, the more they are used and loaded throughout the day, thus distinguishing it from rheumatoid arthritis. With progression in OA, cartilage loses its viscoelastic properties and its ability to absorb load. Generally speaking, the process of clinical detectable osteoarthritis is irreversible, and typical treatment consists of medication or other interventions that can reduce the pain of OA and thereby improve the function of the joint. While drugs and certain cartilage repair procedures may temporarily relieve pain, they often do not treat the underlying problems that led to OA. Conversely, research suggests that if the excess stress on the joint is removed, pain may decrease, and the natural joint tissues may demonstrate some recovery.

A variety of surgical procedures have been developed with the aim of decreasing or eliminating pain and improving function in patients with advanced osteoarthritis (OA). The different approaches include preservation or restoration of articular surfaces, total joint replacement with artificial implants, osteotomy and arthrodesis (fusion).

Arthrodesis are described as being reasonable alternatives for treating OA of small hand and foot joints as well as degenerative disorders of the spine, but were deemed to be rarely indicated in large weight-bearing joints such as the hip due to functional impairment of gait, cosmetic problems and further side-effects. Arthrodesis of the ankle is used as a last resort procedure and is often successful in relieving pain, however, gait and mobility are adversely affected.

Joint replacement is one of the most common and successful operations in modern orthopedic surgery. It consists of replacing painful, arthritic, worn or diseased parts of the joint with artificial surfaces shaped in such a way as to allow joint movement. Such procedures are a last resort treatment as they are highly invasive and require substantial periods of recovery. Joint replacement is sometimes called total joint replacement indicating that all joint surfaces are replaced. This contrasts with hemiarthroplasty (half arthroplasty) in which only one bone's joint surface is replaced and unincompartmental arthroplasty in which both surfaces of the knee, for example, are replaced but only on the inner or outer sides, not both. Thus, arthroplasty as a general term, is an operative procedure of orthopedic surgery performed, in which the arthritic or dysfunctional joint surface is replaced. Alternatively, loading patterns and associated stresses on painful joints can be modified by realigning the joint by osteotomy or other procedures. These procedures are all characterized by relatively long recovery times and are highly invasive procedures.

Other approaches to treating osteoarthritis involve an analysis of loads which exist at a joint. Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. Research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as unloader braces or fixators which control the motion of the bones at a joint. Various of these approaches have had some success in alleviating pain but suffer from lack of patient compliance or lack an ability to facilitate and support the natural motion and function of the diseased joint.

In osteoarthritis of the ankle the cartilage that normally allows the ankle to move smoothly has broken down. When the gliding surface of the cartilage is damaged, the lower ends of the tibia and fibula grind against the top of the talus, creating pain and loss of normal ankle movement. Osteoarthritis can occur in patients due to genetic predisposition and ordinary wear and tear or can be associated with trauma. Trauma related arthritis results when the joint is injured either by fracture, dislocation or damage to the ligaments surrounding the joint. This resulting damage predisposes the joint to osteoarthritis.

Treatments for ankle osteoarthritis include conservative approaches such as weight loss, physical therapy and anti-inflammatory medicine. In more severe cases, surgical interventions including distal tibial osteotomy, ankle replacement or fusion may be required. Ankle replacement is a form of joint replacement where the ankle joints are replaced with artificial joints made from metal alloys and lightweight plastic. Ankle fusion is the other option where the bones of the ankle joint are locked together with screws and plates. Ankle fusion and replacement procedures are characterized by relatively long recovery times and are highly invasive procedures.

There is a need for a treatment modality which bridges the gap between the more conservative approaches such as weight loss, physical therapy and anti-inflammatory medicine and a decision to seek major surgical intervention. Such a treatment modality should be minimally invasive yet sufficiently effective to reduce the pain of osteoarthritis. The treatment should also be compatible with ankle anatomy taking into consideration the tendons and muscles overlaying the ankle joint and relatively thin skin at the ankle. The treatment should not hindering or only minimally hinder normal motion of the ankle joint.

Osteoarthritis of the ankle effects several million in the U.S. According to 2008 estimates, 2.7 million Americans suffered from ankle OA, yet only about 10% of those sufferers underwent surgical intervention to relieve the painful symptoms of OA. Compared with sufferers of hip and knee OA, procedures to treat ankle OA are relatively rarely undertaken. While arthroscopy, ankle fusion, and ankle replacement are treatment options, each can have significant drawbacks.

Ankle fusion, by which pins and/or bone screws are surgically installed in the joint to prevent it from articulating, are a common solution chosen to address ankle OA, but are expensive, result in a loss of joint motion and an abnormal gait, require a long recovery, are irreversible, and involve a very large commitment by the patient and the surgeon. Ankle replacement is complex and in many cases experimental, even more expensive than ankle fusion procedures, and can result in significant complications, have a limited implant lifespan, are also irreversible, and similarly involve a very large commitment by the patient and the surgeon.

External ankle distraction has proven to have great benefits. Some clinical data has suggested a prolonged clinical benefit seven years after completion of the procedure. Typically, there is little to no pain experienced by the patient during the distraction process, which can achieve a significant improvement in range of motion, reversal of OA, cartilage regrowth, bone remodeling, and recovery of joint space. External ankle distraction trusses have been proposed, and two such devices have been commercially available from Small Bone Innovations, Inc. (1380 S. Pennsylvania Avenue, Morrisville, Pa. 19067) as the RingFIX™ and RingFIX™ RAD systems. While those systems have produced some successes, prior external ankle distraction systems greatly inhibit or prevent use of the ankle while the joint is being distracted over many weeks. Because of their unwieldy configurations and the transcutaneous elements (pins, screws, and the like) have resulted in local infection, these systems have seen limited use. Furthermore, because of the complexity of existing systems, the surgical procedure to mount it around the patient's ankle is laborious, and success requires great motivation by the patient to deal with the cumbersome device.

There thus remains a need, unmet by prior systems and methods, for devices and methods for effective distraction of an ankle which suffers from OA, which preserve the ankle joint, are reversible, are less invasive, permit continued use of the ankle during distraction, and are less prone to infection of the patient.

There also remains a need for devices which facilitate the control of load on a joint undergoing treatment or therapy, to thereby enable use of the joint within a healthy loading zone.

The present disclosure addresses these and other needs.

SUMMARY

Briefly and in general terms, the present disclosure is directed towards apparatus and methods for treating the ankle. Various structures are presented to treat ankle pain and more specifically to treat pain associated with osteoarthritis of the ankle joint.

In one aspect, there is disclosed a device useful for distraction of the ankle of a patient, the device comprising a first external member configured and arranged to receive a portion of the patient's leg between the patient's ankle and the patient's knee, a second external member configured and arranged to receive at least a portion of the foot of the patient, wherein the second external member is movable with respect to the first external member, at least one joint connecting the first and second external members in a movable manner which allows the patient to walk and bend the ankle, the joint including at least one spring member, and at least one bone securing element configured and arranged to be implanted through the patient's tibia, fibula, or both, the at least one bone securing element including two ends each of which is configured and arranged to be connected to the first external member, wherein the at least one joint is configured and arranged to at least partially unload the ankle joint by transmitting a portion of the weight of the patient from the first external member to the second external member In another aspect, a method of distracting an ankle of a patient, the ankle joining together one of the patient's lower legs and feet, comprises providing a device as described above, positioning the lower leg of the patient in the first external member, positioning the foot of the patient in the second external member, and generating a distraction force between the first external member and the second external member.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
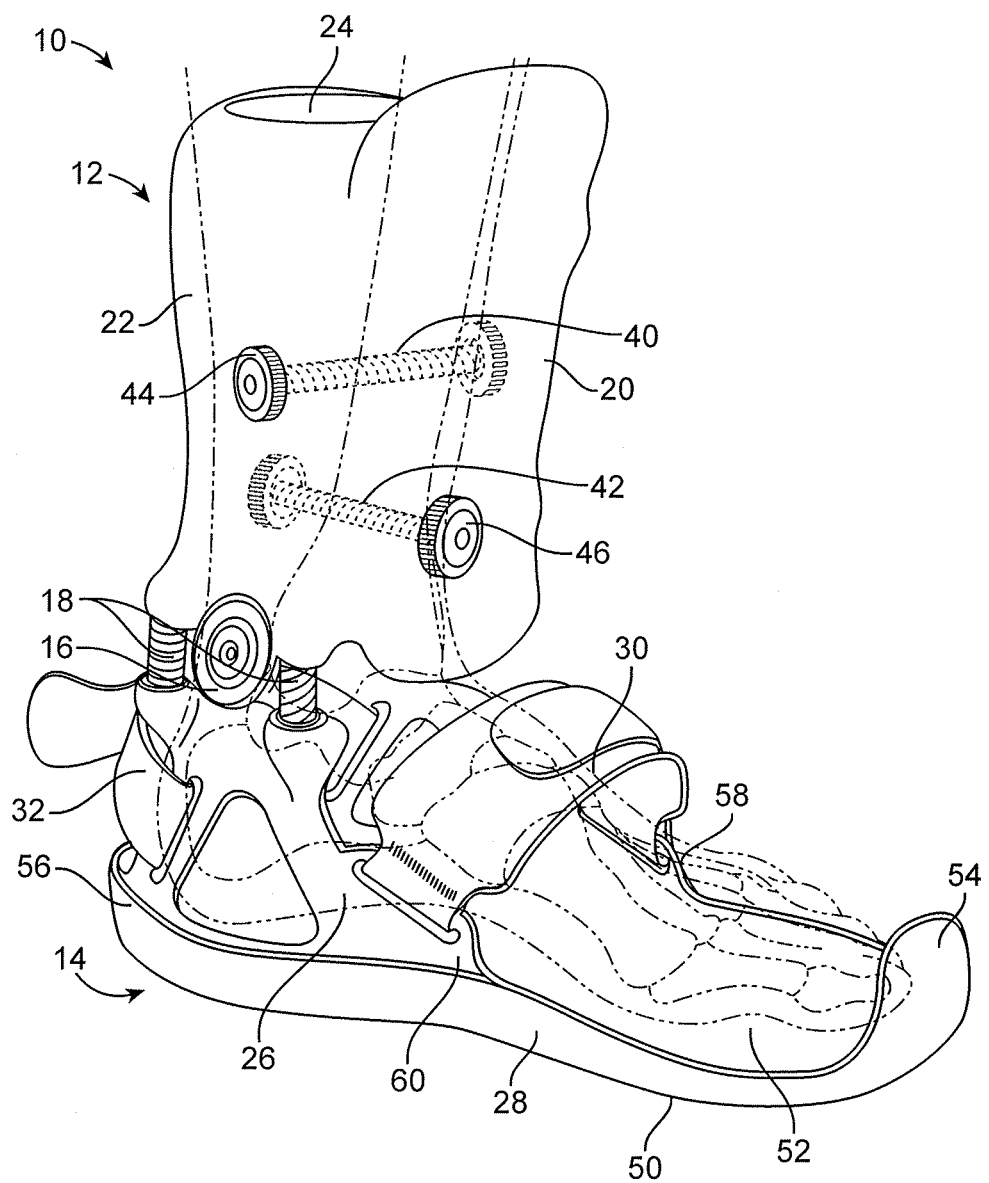
FIG. 1 is a perspective view of an exemplary embodiment of an ankle treatment device.

Referring to the drawing figures, like reference numerals designate identical or corresponding elements throughout the several figures.

Referring now to the drawings, which are provided by way of example and not limitation, this disclosure and the present invention are directed towards apparatus and methods for treating the ankle joint. The devices and methods of this disclosure seek to alleviate pain associated with osteoarthritis of the ankle joint and other pain in the ankle joint. Whereas the devices and methods of this disclosure can be particularly suited to address issues associated with osteoarthritis of a hinged synovial joint, the energy manipulation accomplished by the disclosed apparatus and methods lends itself well to broader applications.

In general terms, footwear is described herein which can address many of the shortcomings of the prior devices and methods for treating ankle pain. While other configurations are within the spirit and scope of the present invention, some exemplary embodiments include pins that are located through the tibia and are attached to a cuff that is configured to be worn around the lower leg (calf and shin) of the patient. Weight-bearing loads are transferred from the cuff through an attached shoe or insole worn by the patient, and to the floor.

This transfer of loads through the shoe and around the ankle joint can be described as load bypassing, where all or some portion of the load normally borne by the ankle joint is transmitted through the footwear to the ground protecting the ankle joint from overloading. In addition to providing load bypassing, the footwear can provided distraction of the ankle joint. When distraction is applied by the footwear, the bones of the foot and leg are separated and a space is created that allows the cartilage and other tissues in the joint to heal. The location of the bone pins and the configuration of the shoe or footwear can be designed to simply bypass load around the ankle joint, or can actually distract the ankle joint creating a space between the bones. Thus, each of the embodiments described herein depending on implementation by the surgeon can act to either bypass all or a portion of the load around the joint or to bypass all of the load and distract the joint. Advantageously, although not necessarily, the footwear is removable by the patient.

The embodiments described herein are designed to accomplish the reduction of symptoms of ankle osteoarthritis for patients using a temporary ankle distraction device. The device can be configured to be fully reversible, provide 40% improvement in pain and function at two years, and have a low complication rate. The ankle treatment device can be achieved effective results with continuous or periodic distraction. One approach is eight weeks of treatment applying distracting force to the ankle joint without displacement. In this way, patient compliance can be optimized. The device can be utilized alone or in conjunction to cartilage stimulation, regeneration treatments, fracture repair or other treatments.

Turning now to the drawing figures, FIG. 1 illustrates a first exemplary embodiment of an ankle treatment device 10 which embodies principles of the present invention. The device 10 includes an upper cuff 12 and a lower shoe 14, which are connected together by one or more rotatable joints 16 on at least one of the sides (medial, lateral) of the device.

The cuff 12 includes a front (anterior) portion 20, a rear (posterior) portion 22 which is joined to the front portion, and a hollow interior 24 which is sized and shaped to receive the lower leg of a patient. Because of anatomical differences between patients, the cuff's portions 20, 22 can be custom-formed for each patient, e.g., by casting the patient's lower leg, detailed measuring, and the like. The interior 24 also optionally, yet advantageously, includes a resilient interior padding (not illustrated).

In order to transmit the load of the patient's weight or a portion of the patient's weight around the ankle from the cuff 12 to the ground or so that the ankle can be distracted by the device 10, the device advantageously includes at least one, and preferably two or more, laterally extending implantable bone securing elements 40, 42, such as bolts, screws, pins or the like which are implanted through the patient's tibia, fibula, or both. The bolts 40, 42 can include threaded ends which extend transcutaneously from the patient, through the cuff 12, and receive nuts 44, 46 on the exposed extracorporeal portions of the bolts outside of the cuff. In other embodiments, not illustrated, the bolts can have plain (unthreaded) magnetic or magnetizable ends, and the nuts 44, 46 are replaced with complementarily shaped magnetic or magnetizable caps; the bolts and caps are designed so that the magnetic force between them is sufficient to hold the cuff between the caps and the patient's lower leg. Other types of connections between the bolts 40, 42 and cuff 12 can include snap fit connections or other known connections.

The bolts 42, 44 advantageously extend in any direction of an anatomical transverse plane through the patient's lower leg below the knee, and when more than one bolt is provided, they can extend in vertically offset transverse planes, as illustrated in FIG. 1. Further advantageously, when multiple bolts are provided, the bolts can extend in generally perpendicular directions, when viewed vertically.

The shoe 14 includes an upper 26 and a sole 28 joined to the upper. Because the upper 26 must transmit the load of the patient's weight between the cuff 12 and the sole 28, the upper is rigid, or includes reinforcing structures which transmit this load without significant flexion. The footwear 10 allows the load or a portion of the load during standing, gait or other activities to be transmitted from the tibia and/or fibula, through the bolts 40, 42, to the cuff 12 and through the pivot joint 16, the upper 26 and the sole 28 to the ground. In this manner, all or a portion of the load can bypass the ankle joint. In the case of complete load bypass, the foot would be hanging in the footwear without any load being applied to the ankle The footwear 10 can also go beyond simply bypassing load around the ankle joint and can apply a distraction force to the joint. To apply distraction, the upper 26 includes a centrally located distraction force transmission member 30, embodied in FIG. 1 as a strap which loops back upon itself from opposite left 58 and right 60 sides of the sole. The strap 30 is configured to be adjustable, and to fit across the top of the patient's foot, and such that it can transmit a distraction force to the patient's foot, e.g., pulling the foot down away from the patient's ankle Similarly, the upper 26 includes a heal force transmission member 32 positioned at the rear of the upper. In the embodiment illustrated in FIG. 1, the upper 26 is open anterior of the member 30 and exposes the patient's toes, although in other embodiments is can be closed. The members 30 and 32 can also be formed like with a ratchet and pawl mechanism, similar in some respects to those commonly used on snowboard bindings. Thus, separate from the isolation of the ankle by the cuff and the shoe, i.e., bypassing the load of the patient's weight around the ankle to the sole of the shoe, the device 10 can apply a distraction (downward) force to the patient's foot which is independent of the isolation of the ankle.

The sole 28 includes an outsole 50, and insole 52, a toe portion 54, and a heal portion 56, which are formed in known ways to fit the foot of a patient. Although the footwear 10 is shown in the form of a shoe, the footwear can also be formed in a low profile version which fits within a shoe and is therefore considered a shoe insert.

In the version of FIG. 1, bridging the cuff 12 and the shoe 14 is at least one, and advantageously several, coil springs 18. As will be readily appreciated, when in use the springs 18 force the cuff 12 and shoe 14 away from each other returning the footwear to a neutral position after pivoting at joint 16. Other devices can be used instead of coil springs, as will be immediately apparent, such as leaf springs, air pistons, flat or Belleville springs, and the like. While the exemplary embodiments illustrated herein show only two springs 18, because FIGS. 1-3 are right front top perspective views, additional springs 18 are also advantageously provided on the left side of the device 10 in a symmetrical manner.

The arrangement of the pivot 16 can allow the load bypassing support to change as the ankle joint articulates. For example, the load absorption can be at a maximum between ±5 degrees of flexion and can be at a minimum or at zero beyond some larger degree of flexion, such as ±15 degrees. In another example, load absorption can be active throughout the entire range of motion of the typical gait cycle.

Although the load absorbing device is active in applying a load bypassing force during only a portion of the range of motion of the joint, the device should be arranged to permit a full or nearly full range of motion. During a portion of the range of motion the device can be in a passive or inactive state. In one example, the footwear device 10 permits a full natural range of motion including 50° of motion in plantarflexion, 20° of motion in dorsiflexion, 20° range of motion in abduction, 35° of motion in adduction, 25° in internal and external rotation.

Figure 2:
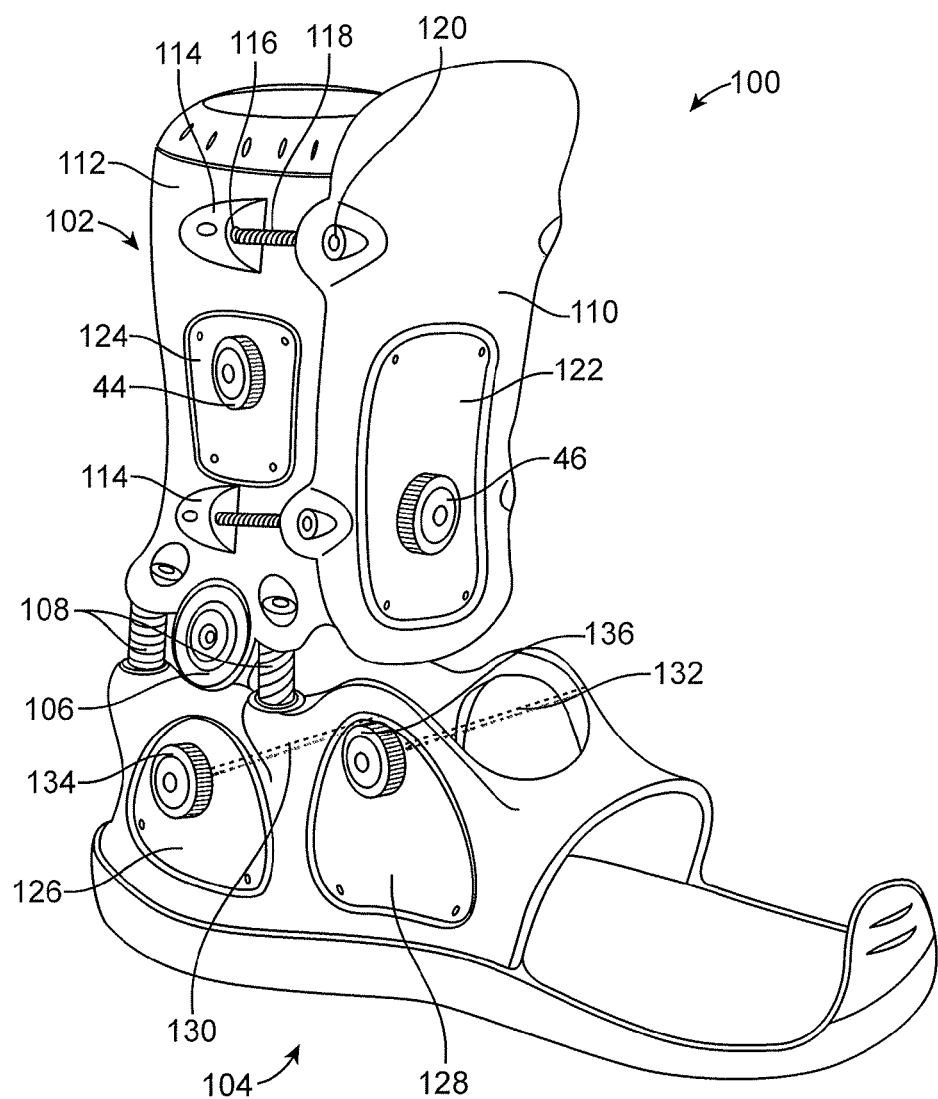
FIG. 2 is a perspective view of a second exemplary embodiment of an ankle treatment device.
Figure 3:
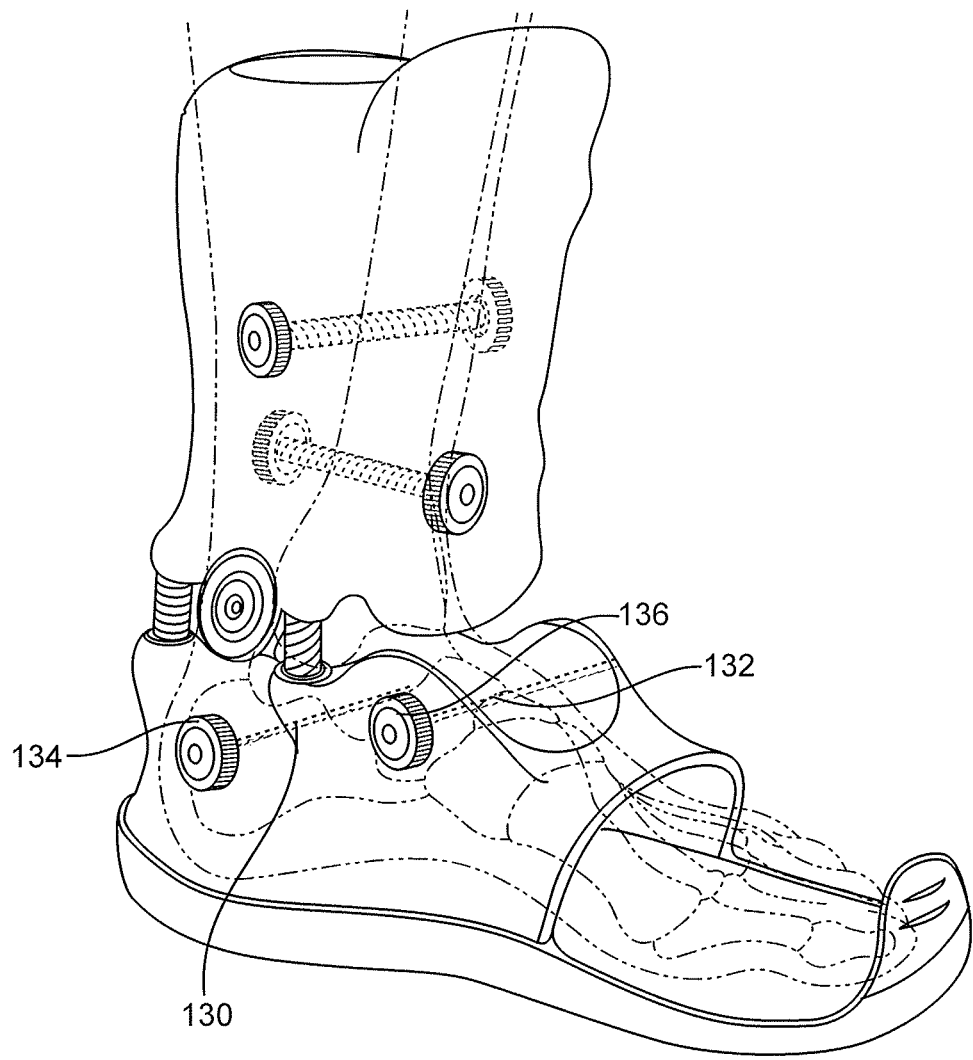
FIG. 3 is a perspective view of a third exemplary embodiment of an ankle treatment device.

FIG. 2 illustrates another exemplary embodiment of a footwear device 100 which is similar in some respects to that illustrated in FIG. 1 and described elsewhere herein. The device 100 includes a cuff 102, a shoe 104, a joint 106, and springs 108, here embodied as coil compression springs.

The cuff 102 is formed of at least two portions that are adjustably joined together, so that the hollow cuff can be tuned to fit the patient's lower leg. More specifically, the cuff 102 includes a front portion 110 which is configured to bear against the patient's shin, and a cuff rear portion 112 which is configured to envelop the rest of the patient's lower leg, including their calf. The front 110 and rear 112 portions are joined together by at least one, and preferably several adjustment mechanisms 114 which extend between the two portions. The adjustment mechanisms can take any of numerous configurations, only one of which is described here. By way of example and not of limitation, the mechanisms can include a threaded insert 116 attached to one of the two portions 112, 114, and a threaded shaft 118 with a drive head 120 which mates with the insert 116. With the drive head 120 captured by the other of the two portions 112, 114 (e.g., in a hold or recess), rotation of the drive head, and therefore of the shaft 118, pulls the front portion 110 towards the rear portion 112 (for one direction of rotation), and thus tightens the cuff on the patient's leg. Instead of a threaded connection, ratcheting mechanisms, buckles, e.g., such as those commonly used on snow ski boots, can be used. While only two mechanisms 114 are illustrated in FIG. 2, it is advantageous that both the left and right sides of the cuff 102 are provided with such mechanisms.

The cuff 102 also optionally includes one or more bearing plates 122, 124, against which the nuts 44, 46 bear. The plates 122, 124, can be formed separately from and of a different material than the rest of the cuff 102, e.g., one more capable of transmitting the compressive load from the implanted bolts and extracorporeal nuts. The plates 122, 124 fit into correspondingly configured openings in the cuff so that the plates capture the cuff front, rear, and side portions and force them against the patient's lower leg. While only front and right side plates are illustrated, rear and left side plates are also optionally provided, and optionally for all implanted bolts.

In the embodiment of FIG. 2, instead of the force transmission portions 30, 32 of FIG. 1, implanted bolts 130, 132 and nuts 134, 136 can be used to secure the shoe to the patient's foot. The bolts 130, 132 are advantageously implanted horizontally, i.e., medial-laterally in an anatomical transverse plane, between the left and right sides of the patient's foot. Similarly, the shoe 104 can include plates 126, 128, for nuts 134, 136.

With reference to FIG. 3, the bolts 130, 132 are better illustrated extending medial-laterally. Instead of bolts, implanted wires or screws can be used. These fasteners can go part way or all the way through the talus.

Figure 4:
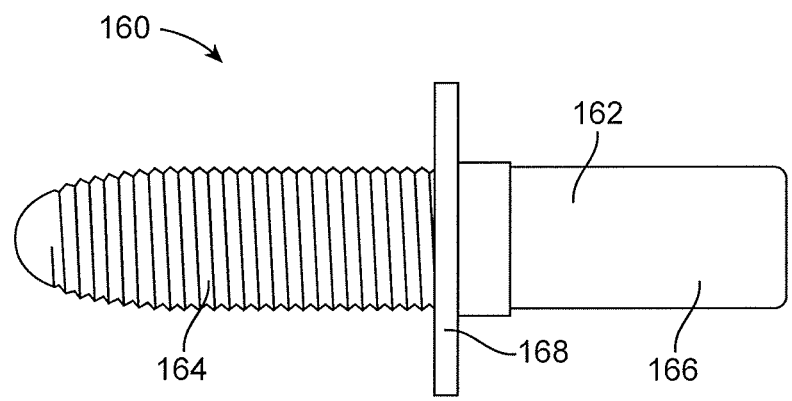
FIGS. 4 and 5 are side and top views of an exemplary implantable portion of an ankle treatment device.
Figure 5:
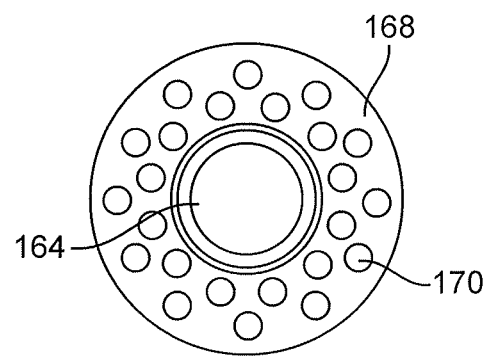

FIGS. 4 and 5 illustrate two views of an alternative to the implantable bolts described elsewhere herein, namely, transcutaneous anchors 160. The anchors 160 each include a shaft 162 having a threaded distal portion 164, which is entirely implanted in the patient's lower leg, e.g., in the tibia, fibula, or both. A plain or unthreaded proximal portion 166 is opposite the threaded portion 164. A radial flange 168 is positioned between the two portions 164, 166, and can be formed of the same material as the shaft, or of a different material. The flange 168 or other anchoring structure allows suturing to the skin.

As with the implanted bolts described elsewhere herein, the transcutaneous anchors 160 cooperate with extracorporeal caps or the like to capture the cuff of the distraction device against the patient's lower leg, while transmitting all or a portion of the load applied to the ankle by the weight of the patient through the ankle treatment device 10 bypassing or partly bypassing the patient's ankle joint.

As the bone anchors 160 are designed to traverse the skin of the patient, certain precautions can be implemented to prevent the transmission of microorganisms at the skin penetration site. In one embodiment, the anchors 160 can have a coating to reduce the possibility of infections, for example, titanium anchors can be provided with a silver anti-infective coating. Other known coatings and precautionary methods can also be used. Other precautions for prevention of infection can include specific cleaning and maintenance steps to be performed by the patient. For example, adhesive coverings may be provided for the exposed ends of the bone anchors when they are not in use.

In another embodiment, a porous tissue cuff can be secured around the bone anchors 160 to prevent infection at the tissue penetration site. A tissue cuff can be secured to the bone anchor 160 and promotes skin growth into the cuff to provide a barrier to microorganisms. The bone anchors can also include flanges or other anchoring structures which allow suturing to the skin. The flanges 168 on each of the anchors are arranged to lie just below the surface of the patient's skin. The flanges 168 can be provided with small openings to accommodate sutures for securing the skin around the anchors. Alternatively, other known skin securing systems can be used to secure the skin to the anchors.

The bone anchors 160 as described herein can be designed to have a top surface which does not protrude from the surface of the skin to prevent any discomfort of protruding parts when the device is removed. Alternately, other anchor structures can be used which protrude somewhat from the bone, however, preferably the bone anchors do not protrude more than about 5-10 mm from the skin surface.

Figure 6:
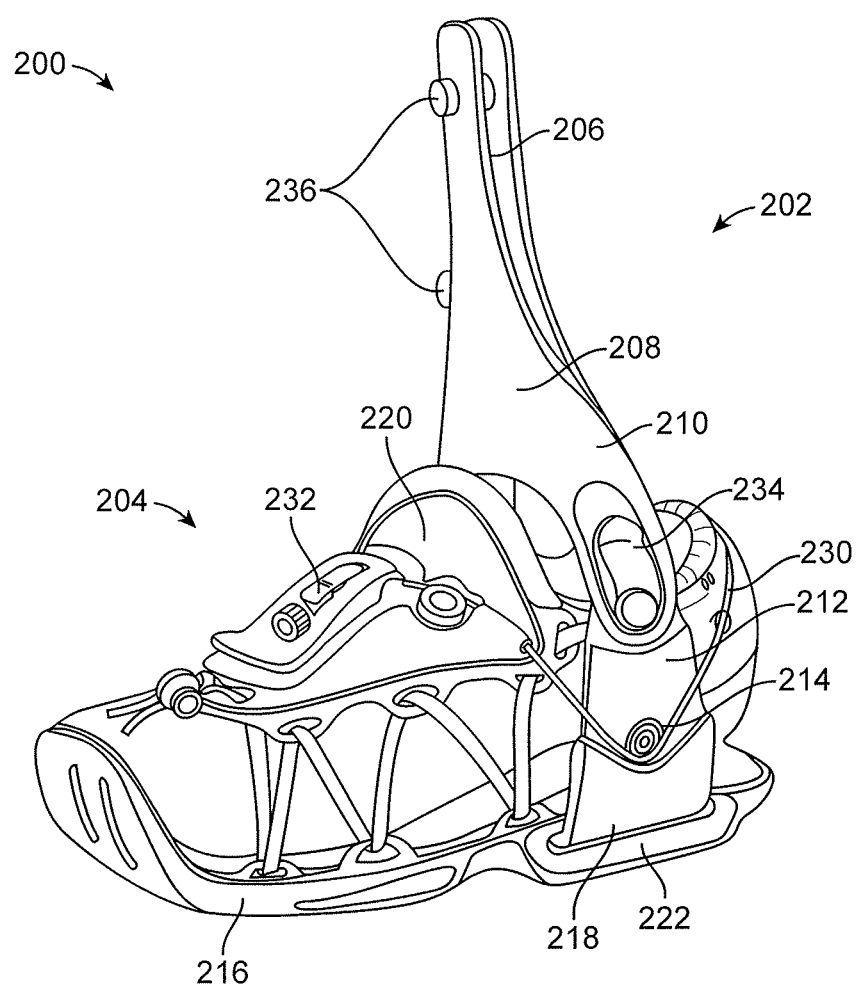
FIG. 6 is a perspective view of fourth exemplary embodiment of an ankle treatment device.

FIG. 6 illustrates yet another exemplary embodiment which is similar in some respects to other embodiments described herein. In general terms, the embodiment of FIG. 6 is a fixator-orthotic hybrid, by which all or part of a patient's weight (load) can be transferred directly to the ground, and includes a separately operable, and therefore optional, distraction system. Because the embodiment of FIG. 6 does not require (but optionally may include) distraction pins, wires, screws, or the like implanted in the foot of the patient, the shoe portion of the device can be configured to be removable by the patient.

Turning now to the drawing, the device 200 includes an upper wishbone 202 which is configured to be attached to the lower limb of a patient, e.g., to the patient's tibia, and a lower shoe or footwear 204, which is configured to receive the patient's foot. The wishbone 202 includes an upper portion 206 which receives implanted pins, wires, screws, or the like, 236 which secures the wishbone to the patient's lower limb in a manner similar to corresponding structures described elsewhere herein. As described elsewhere herein, the pins 236 preferably have a sub-dermal flange to prevent epidermal downgrowth and bacterial migration. The wishbone 202 includes a lower portion 208 which includes a pair of laterally spaced apart arms 210, one of which extends down and laterally and the other which extends down and medially, so as to span the top of the foot of the patient. A load-to-ground load extension bracket 212 extends downward from each arm 210, and includes portions of a joint or pivot 214. As with other embodiments described herein, the pivot 214 permits the patient's ankle to flex, and optionally can be configured to restrict the range of motion of the ankle.

The shoe 204 includes a sole 216 and a sole extension 218 which extends upwardly from the sole and connects with the bracket 212 at the pivot 214, with the sole extension including portions of the pivot. The shoe 204 also includes an upper 220 which is configured to receive and transfer a distraction force to the patient's foot in a manner similar to other embodiments herein. A cushion 222 is optionally provided in the sole 216, which absorbs some of the impact or shock from be transferred directly from the sole to the patient's lower limb.

The device 200 includes a distraction force transfer cable 230 which, when tensioned, applies a distraction force or downward force to the patient's foot. The provision of a force transfer cable, instead of implanted pins, screws, or wires in the foot, can have numerous advantages, including that there is no structure that is implanted in the patient on the foot side of the ankle joint. In the exemplary embodiment, the cable 230 extends over the top of the patient's foot passing through portions of the upper 220, and also passes over and around the patient's heel by passing through portions of the upper which overlie the patient's heel. For this purpose, the upper can be provided with eyelets, loops, channels, holes, and the like, so that the cable does not slide relative to the upper 220. Advantageously, although still optionally, the device 200 includes a cable tensioning mechanism 232, which is configured to put the cable 230 in tension and to adjust the tension in the cable. While numerous known cable tensioning mechanisms are usable, one exemplary mechanism 232 includes a threaded bolt with an accessible head which, when turned, pulls the cable tighter relative to the upper. The cable 230 is advantageously led around the pivot 214, so that any distraction force applied to the patient's ankle by the cable is not significantly affected by the angular orientation of the ankle Further optionally, the wishbone 202 includes a quick release clip 234 between each of the arms 210 and each of the transfer brackets 212, to allow the patient to remove the footwear while leaving the wishbone 202 attached to the leg. Such clips are well known.

The device 200 of FIG. 6 can have numerous advantages. As described above, no bone pins are used on the foot side of the joint or pivot, which is thus less invasive for the patient. The load (patient's weight) can simply bypass the ankle joint by passing through the wishbone to the bottom of the shoe, i.e., the foot can be dangling and have little or no weight bearing. The device 200 includes a separate mechanism for distraction of the ankle, which is provided by a cable system which pulls the patient's foot down and away from the wishbone, and therefore away from the patient's lower limb. Thus, without the distraction system, the device 200 functions to bypass the weight load, but the ankle's bones still may be touching. When provided with the distraction cable system, the bones of the ankle can be separated both at rest and during loading. Furthermore, the wishbone is removable from the patient's tibia at the pins, which the device still includes a fixed pivot.

With reference to the several drawing figures, exemplary methods of distracting the ankle of patient will now be described. Initially, for the embodiments in which implanted bolts, wires, or anchors are used to transmit force to and from the patient, the bolt(s), wire(s), and/or anchors are implanted in the positions described elsewhere herein. The patient's foot is then positioned in the shoe of a distraction device, e.g., one of those of FIGS. 1-3 and 6. In the embodiment of FIG. 1, the force transmission portions 30, 32 are tightened so that the patient's foot is securely held in the shoe and against the insole; for that of FIG. 6, the cable 230 is similarly tightened. In the embodiments with an adjustable cuff, the cuff is adjusted, e.g., with the adjustment mechanisms, so that the cuff can transmit force from the bolts, wires, and/or anchors to the patient's lower leg. The pins are positioned so that a desired amount of load bypassing and optionally distraction are achieved. In one variation, the amount of load bypassing is adjustable by adjustment of the footwear.

In embodiments in which the shoe is not attached to the patient's foot with pins, screws, wires, or the like, e.g., the embodiment of FIG. 6, the shoe is placed on the foot in a typical manner. Because the shoe is firmly attached to the patient's foot, preventing the patient's foot from moving upward relative to the shoe insole, and because the cuff is attached to the patient's lower leg, preventing the cuff from sliding up the lower leg, the force generated by the distraction force generating members provides distraction of the ankle joint. The load of the patient's weight, however, is partially or entirely transferred around the patient's ankle, by being transferred via the cuff from the lower leg, through the joint, and through the shoe sole to the ground. In some embodiments, because the distraction force generating structures work separately from those which transfer load (weight) around the ankle, a separate and therefore optional step includes adjusting the device so that a distraction force is generated and applied to the patient's ankle. Furthermore, a distraction force can be distributed over multiple portions of the patient's foot, e.g., can be applied to the top of the foot and the heel, which can therefore put less stress on those portions of the foot.

Figure 7:
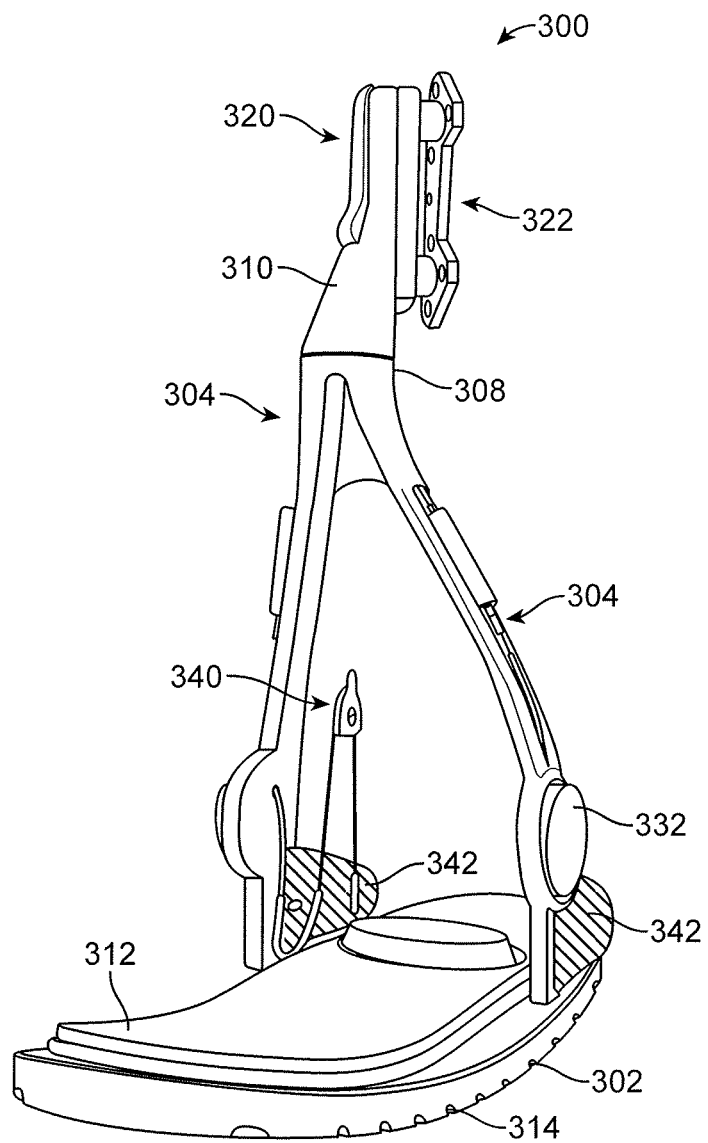
FIGS. 7 and 8 are perspective views of a fifth exemplary embodiment of an ankle treatment device.
Figure 8:
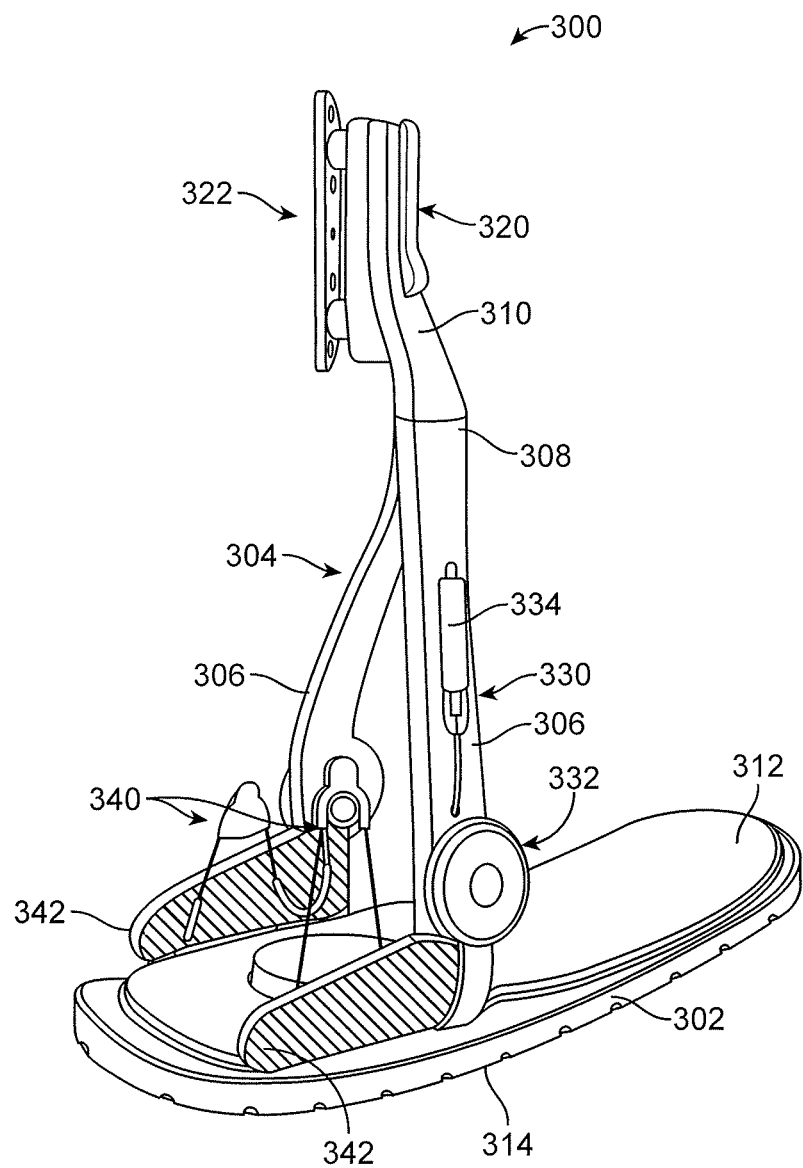

Turning now to FIGS. 7 and 8, there is shown yet another approach to an ankle treatment device 300. As shown in FIGS. 7 and 8, the ankle treatment device 300 includes a sole or platform 302 for receiving a patient's foot, and an upper wishbone frame 304 projecting vertically from the sole 302. The frame 304 includes a pair of arms 306 attached to lateral sides of the sole, and which join at a junction 308 to form a single member 310. The arms 306 are curved in a manner to provide a space for the patient's lower leg and the single upper member 310 is configured to reside along an exterior of one side of the lower leg. In one particular approach, the single member 310 is sized and shaped to reside along an interior of a patient's lower leg. The sole 302 can be further contoured to comfortably receive a foot and further include one or both of a cushion 312 configured on an upper surface of the sole 302 and treads 314 on a lower side of the sole 302. The ankle treatment device 300 is formed without a pivot between the wishbone frame 304 and the sole 302. Flexibility of the ankle joint is accommodated by flexibility of the cable tensioning portion of the device.

The upper member 310 of the ankle treatment device 300 can be further provided with a quick release and attachment mechanism 320 to allow the wishbone frame 304 to be removed by the patient or the physician. The quick release 320 connects the upper portion 310 of the wishbone to two connection buttons extending through the patient's skin. These two external buttons are rigidly fixed to a subcutaneous bone anchor receiving structure or plate 322 implanted longitudinally along the tibia and secured by suitable bone anchors to the tibia.

Adjustable distraction of the ankle is provided by two tension assemblies 330 provided along one or both of the vertically projecting arms 306 as shown in FIG. 8. The tension assemblies 330 apply a tensile force to the talus to distract the ankle joint. To connect the tension assemblies to the talus, a talus pin (not shown) is inserted through the talus as will be described below and a portion of the talus pin in the form of connection button extends through the skin of the patient. One or more talus pin connector assemblies 340 are provided to connect to the external buttons of the talus pin. Tension cables extend from the talus pin connectors 340 through lateral foot supports 342 of the sole 302 and to a tension adjustor 332. Rotation of the tension adjustor 332 increases or decreases a distraction force on the ankle joint. A tension indicator 334 can be provided to provide an indication of the tension applied by the tension assembly 330.

Figure 12:
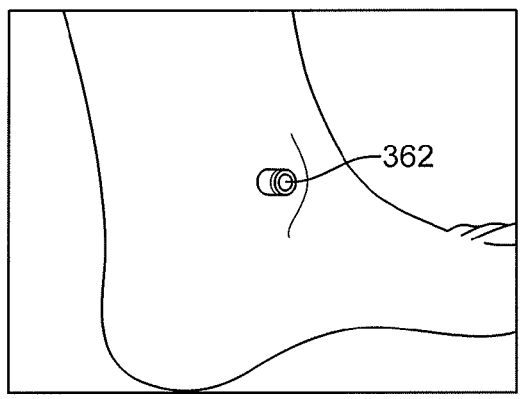
FIG. 12 is a side view, depicting an external cleat attached to the implanted portion shown in FIG. 11.
Figure 13:
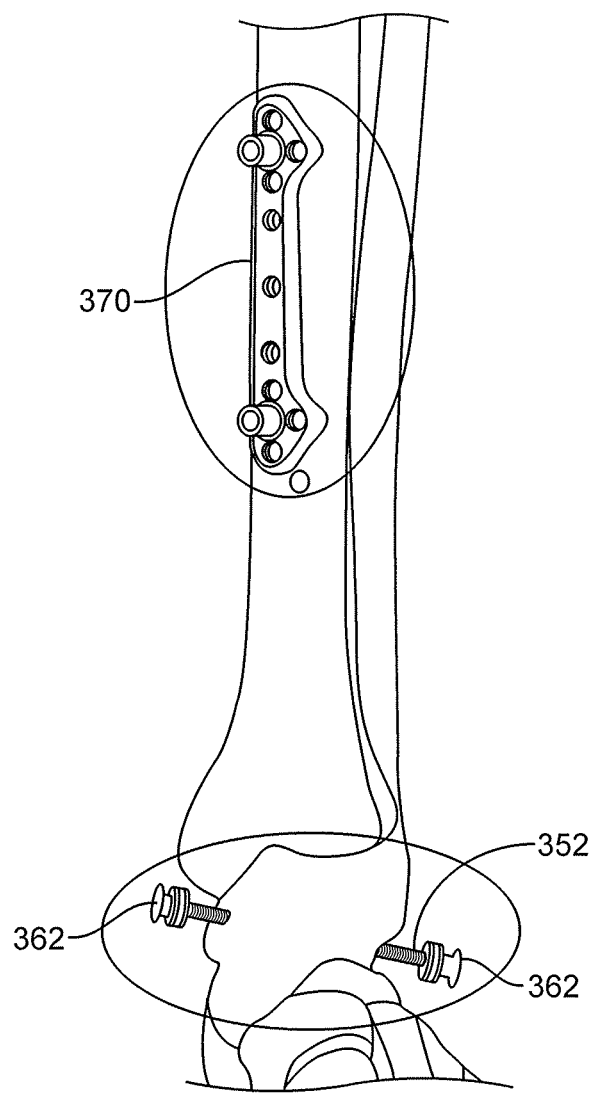
FIG. 13 is a side view, of the embodiment of FIGS. 7 and 8 depicting a talus pin projecting through a patient's skin and an implanted bone plate.

Referring now to FIGS. 9A-F, a procedure for implanting and fitting the ankle treatment device 300 is described including exemplary instruments for performing the procedure. However, similar procedures can be used for the other embodiments described herein. In a first step in one treatment approach, a correct location for a talus pin 352 is determined. In this regard, a drill guide 354 with radiopaque rings 356 is placed about a patient's talus bone 358. Using fluoroscopy or other imaging technology, the desired landing site is ensured by viewing the radiopaque rings 356. Once the proper positioning has been achieved, a drill 360 is employed to advance the talus pin 352 through the talus 358 and out through an opposite side of the patient's skin. Next, talus buttons 362 are threaded or otherwise advanced along the talus pin 352, and placed tight against the patient's skin (See FIGS. 9B, 12 and 13). Excess length of the talus pin 352 can be removed.

Figure 9A:
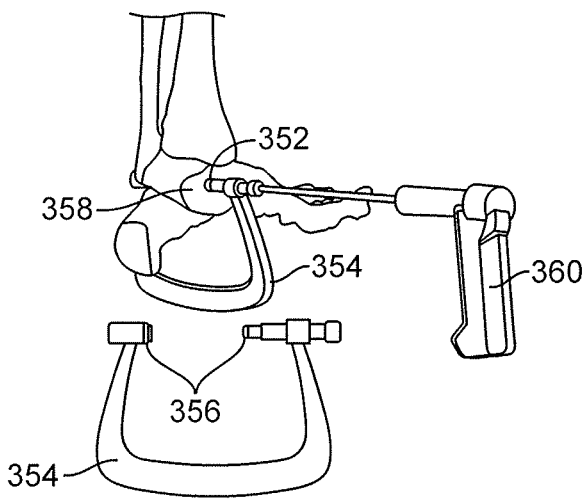
FIGS. 9A-F are various views depicting one approach to implantation of an ankle treatment device.
Figure 9B:
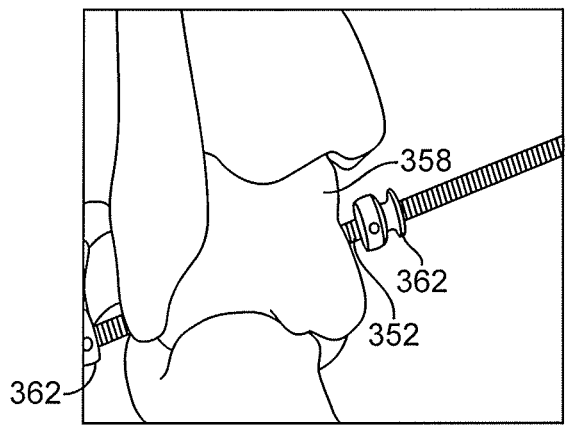
Figure 9C:
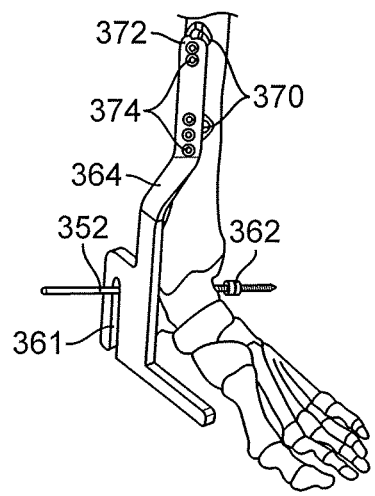
Figure 9D:
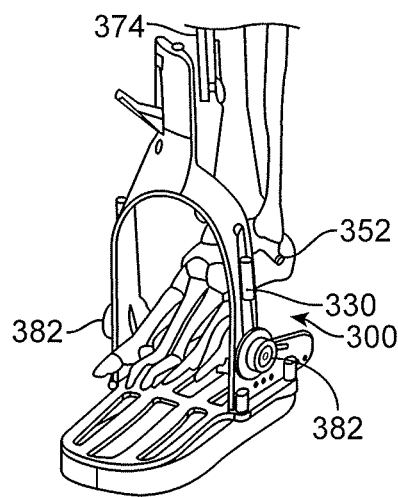
Figure 9E:
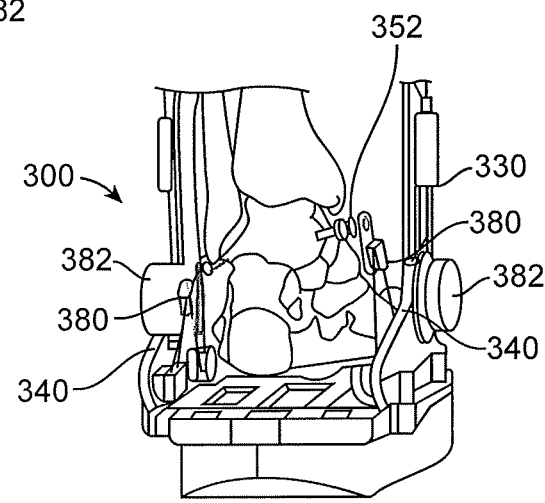
Figure 9F:
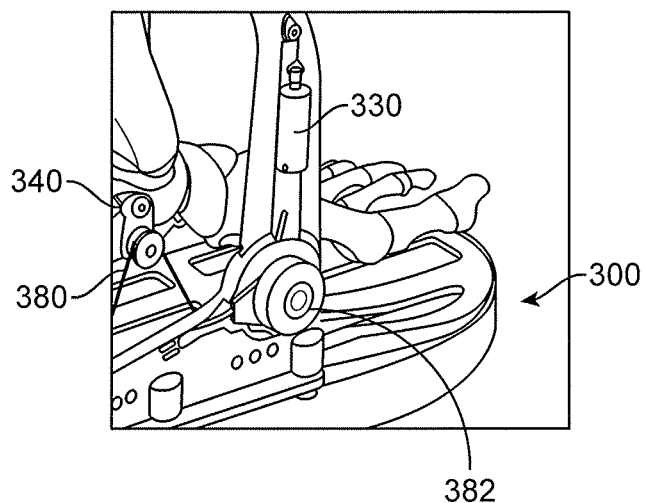
Figure 10:
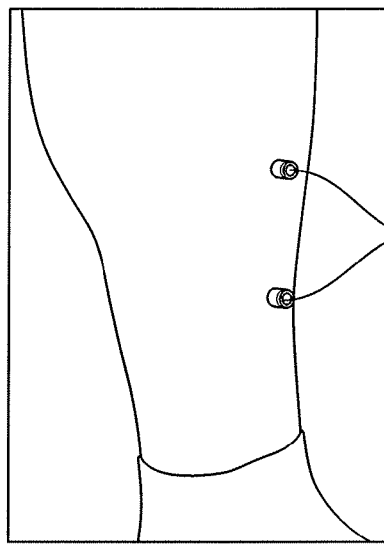
FIG. 10 is a front view, depicting implanted portions of the embodiment of FIGS. 7 and 8.
Figure 11:
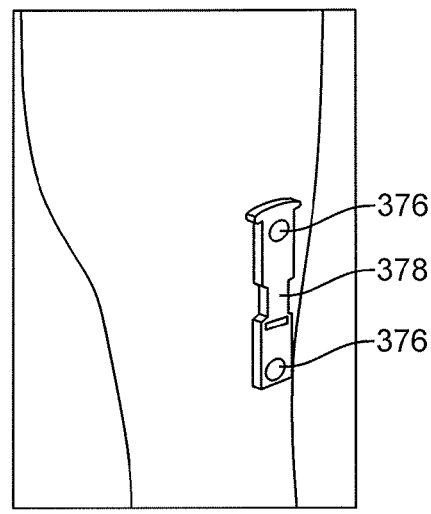
FIG. 11 is a side view, depicting portions of the implanted portion extending through a patient's skin.

A bone plate attachment fixture 364, as shown in FIG. 9C, is then provided and used to determine a height and alignment of a subcutaneous bone anchor 370, which has been placed against the tibia using conventional means but not yet secured in place. To accomplish proper placement, the fixture 364 includes a slot 366 for receiving a portion of the talus pin 352. Threaded projections 372 of the bone plate (See also FIG. 13) are received in openings 374 formed in an upper portion of the fixture 364, to thereby facilitate properly locating the subcutaneous bone anchor 370 with respect to the talus button 362 located on the treatment side of the leg. Finally, screws 376 are employed to both attach the subcutaneous anchor 370 to bone as well as attach an external cleat 378 (See FIG. 11) to the bone anchor 370. The external cleat 378 can be used in place of one or more buttons as an upper quick release platform for the ankle treatment device 300 (See FIG. 13).

Figure 14:
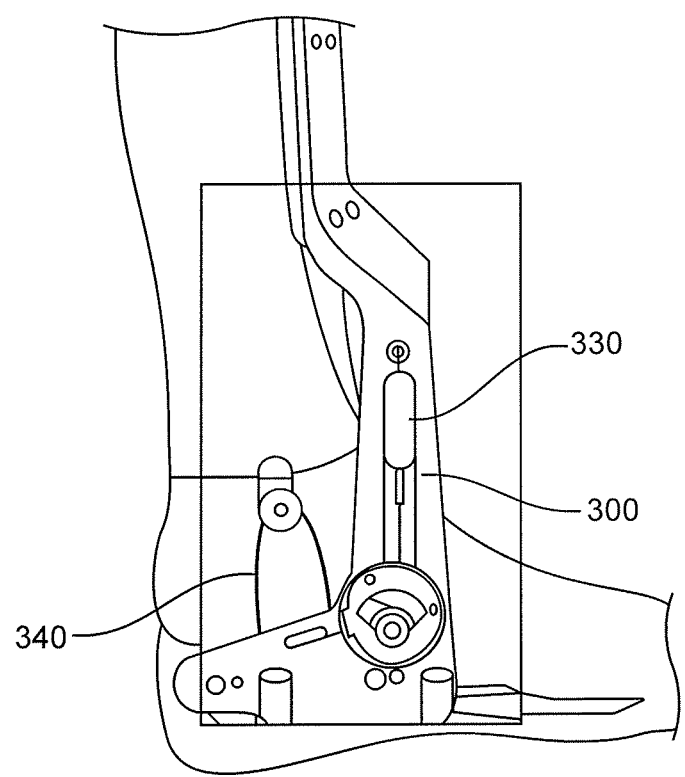
FIG. 14 is a side view, depicting the ankle treatment device of FIGS. 7 and 8 attached to a patient's body.

To attach the treatment device 300 to the patient's leg, the quick release and attachment mechanism 320 is first attached to the external cleat 374. Thereafter, the talus pins 352 are presented for attachment to the talus pin connector assemblies 340 of the treatment device 300 (See FIGS. 9D-F). Here, a pulley assembly 380 of the talus pin connector assemblies 340 are connected to the talus pins 352. Thereafter, distractor reels 382 of the adjustable distractor tension assembly 330 are turned until a desired distraction force is achieved. In this regard, the assembly can include color or other indicators 334 reflecting proper tensioning. FIG. 14 depicts the treatment device attached to the patient's leg. As stated, multiple device attachment and removal is contemplated, such as detachment for bathing or sleeping.

Further, in various approaches, it may be desirable to separately or additionally unload body weight with a mechanism separate from the mechanism provided for distraction of the ankle or other joint. Body weight and/or gait loading on a joint can be high, and as much as 500 lbs. or more. Distraction force in an ankle joint need only be 10 lbs of tension for certain treatment purposes. Thus, approaches to unload body weight with a mechanism separate from the mechanism provided for distraction of an ankle joint are contemplated.

Figure 15:
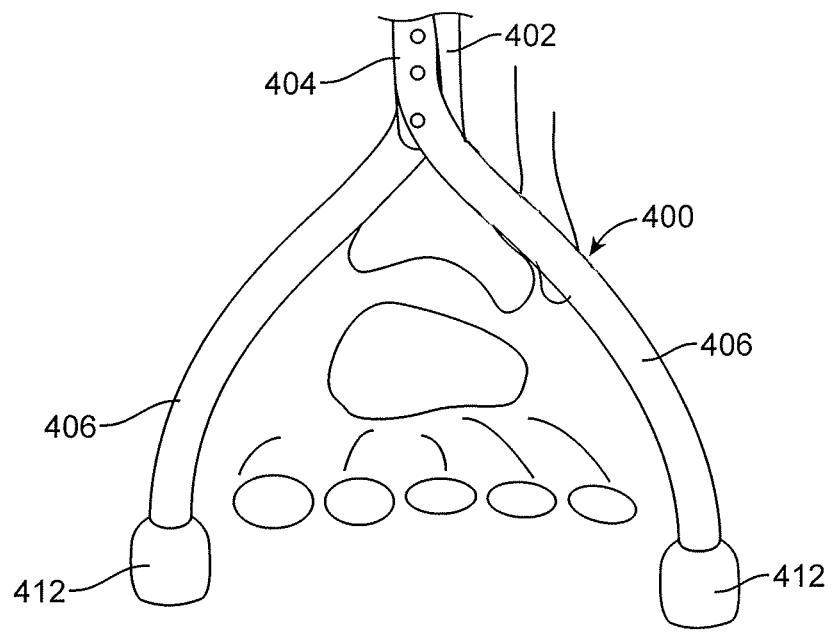
FIG. 15 is a front view, depicting a body weight off-loading device.

In one approach to unload an ankle joint of body weight (See FIG. 15), a wishbone frame unloader brace 400 is provided and removably attached to a tibia 402. An upper portion 404 of the frame includes through holes sized to receive anchoring screws. Extending from the upper portion 404 are a pair of spaced members 406 that are sized and shaped to both accommodate a width of a patient's foot 408, and to extend to or beyond a bottom of the foot and engage a walking or traveling surface. In this way, the tibia 402 absorbs body weight forces to the exclusion of the ankle and foot. Terminal ends 412 of the frame 400 can be equipped with structure facilitating a stable engagement with a traveling or standing surface. Thus, the body weight of the patient as well as the gait forces normally transmitted through the ankle joint during gait are both transmitted directly to the ground or footwear protecting the ankle joint from overloading. The wishbone frame unloader brace 400 may be used alone or in combination with a distraction device such as those illustrated in FIGS. 1, 6 and 7.

Figure 16:
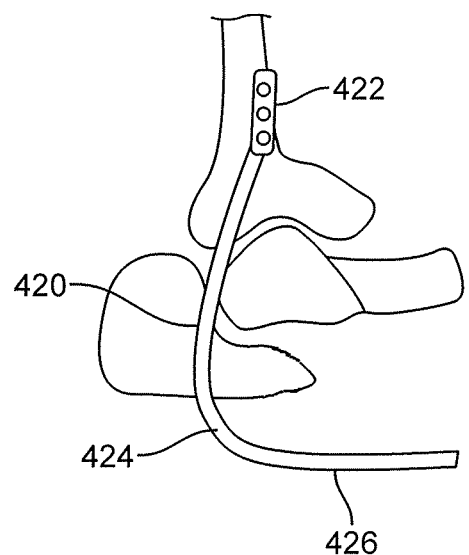
FIG. 16 is a side view, depicting another approach to a body weight unloading device.
Figure 17:
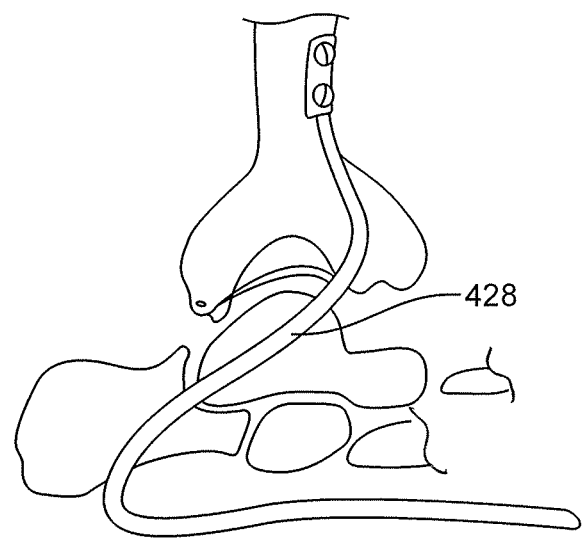
FIG. 17 is a side view, depicting yet another alternative embodiment of an unloading device.
Figure 18:
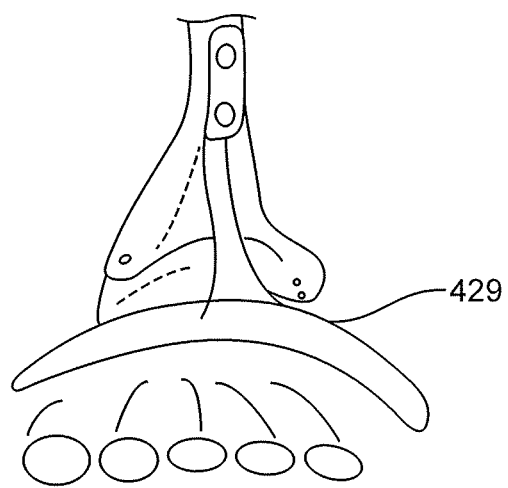
FIG. 18 is a front view, depicting an unloading device configured to cooperate with a top of a patient's foot.

In another approach, a removable body weight unloading device can be embodied in a generally L-shaped member 420 (FIG. 16). An upper portion 422 of the device 420 is adapted to be affixed to a patient's tibia, and a lower portion 424 can be curved to define a horizontal platform 426 for engaging a traveling surface. As so configured, the device 420 acts as a spring to unload body weight forces during gait or standing. A S-shaped 428 or other curved member are also contemplated (See FIG. 17) which can act as a spring. In another approach a lower portion 429 of the unloading device engages a top of a foot (See FIG. 18).

It is to be recognized that rather than attaching a body unloading device to the tibia, an external cuff can be alternatively or additionally employed for affixation to a patient's leg, above or below the knee. An external cuff approach, of course, avoids a need for skin and bone penetration. In a particular approach of an external cuff, the cuff can be configured to fit around a calf, knee, thigh and bent knee, and can be custom fit to a patient. One or more tightening bands can be further provided to ensure proper fit about soft tissue.

Moreover, in yet another approach, a lower portion of a body weight unloading device can attach to a sole structure for receiving a patient's foot. Thus, body weight forces are transferred from the sole structure to the tibia directly, or in this case of a device with an external cuff, the forces are accommodated by the cuff.

Figure 19:
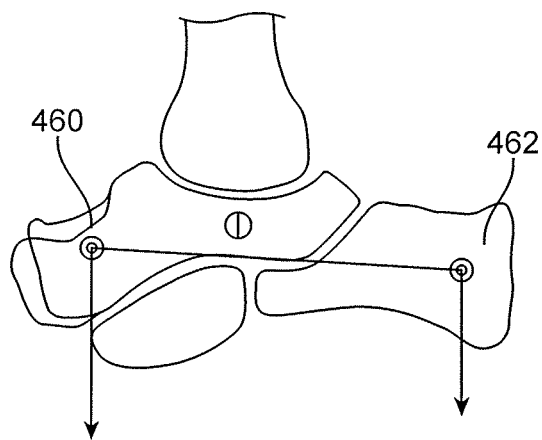
FIG. 19 is a side view, depicting various alternative bone attachment positions.
Figure 20:
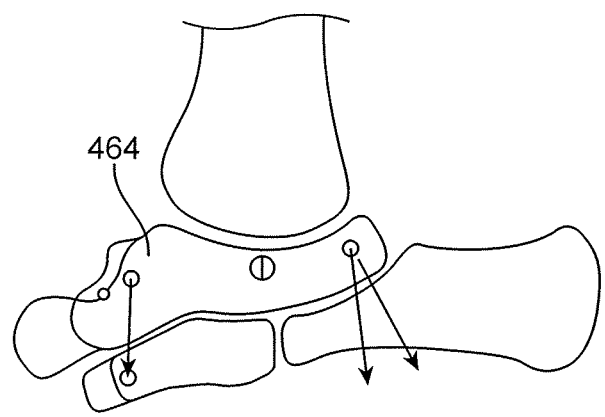
FIG. 20 is a side view, depicting yet further bone attachment positions.

It has also been contemplated that where a single talus force connection is deemed not viable for desired body weight unloading, tension can be applied on multiple bones of the ankle or foot. Thus, it is contemplated for example, that tension can be applied on a talus neck 460 and calcaneus bone 462 to result in desired distraction of the talus along the tibial axis (See FIG. 19). Other approaches (See FIG. 20) can involve employing two attachment points to the talus 464, or a single off-center further attachment point. Accordingly, a tension axis can be adjusted an optimized through the selection of tension attachment points. That is, positioning attachments along various axes of the foot determine the movement arm for unloading magnitudes of tension or a plurality of attachment ports can be likewise varied to achieve proper magnitudes of tension as well movement arms. Moreover, tension can be pulled on medial or lateral sides of bone connections as can anterior and posterior positions with different magnitudes of tension to achieve desired unloading.

Numerous modifications and additional, optional features can also be included. By way of example, the cuff could be built in a limited number of sizes, or be custom fabricated for each patient. The bearing plates could be drilled when the bolts and/or wires are installed; they could be custom-formed inserts which are then installed into prefabricated cuff shells; and they could be fabricated directly into the cuff and the shoe. A dynamic distraction force generating member, such as a spring or a static mechanism, such as a simple threaded bolt, could be used to generate a distraction force on the ankle, and can permit tuning the distraction force. The joint can be configured to allow or limit the range of motion of the patient's ankle, e.g., by the inclusion of stops in the joint. The distraction force generating members can optionally be detachable from the cuff, the shoe, or from both to allow the periodic adjustment of the distraction force depending on patient recovery, activity level or other variables.

The ankle treatment devices described herein can exert the distraction force on the ankle joint throughout its range of motion or through only a portion of the range of motion of the ankle joint. The physician can determine the unloading range of motion for the particular patient as well as how much to unload the ankle based on certain characteristics of the patient injury or disease.

As described in U.S. Provisional Patent Application No. 61/504,886, filed Jul. 6, 2011, and incorporated herein by reference in its, entirety a physician can make a treatment decision about whether the ankle distracting device should be used for a particular patient based on estimates of contact stresses in the ankle The use of the distracting device may be to treat a joint that has diagnosed OA disease or if used at the time of ankle fracture to prevent the onset of disease by allowing the ankle to heal without contact stresses above the threshold of 1.3 MPa-s. The time period for temporary use of the distracting device may depend on a combination of joint status, patient demographics and device load absorption and may range from about 4 weeks in some instances to a period of about 6 months to 2 years. In one application, the device may be used for a period of 6-12 weeks for treatment of osteoarthritis.

For the general population, it is expected that a force reduction of approximately 10-40 pounds could be effective in the reduction of pain across an ankle joint. A 30 pound reduction in force would work well for one size fits all load absorbing device designed to fit a majority of patients. Alternatively, a modular system can be provided with different springs available for fitting a patient based on the finite element stress analysis of the patient's particular joint or based on other patient characteristics including weight and activity level.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

We claim:

1. A device useful for treatment of the ankle joint of a patient, the device comprising:
   a first external member configured and arranged to receive a portion of the patient's leg between the patient's ankle and the patient's knee;
   a second external member configured and arranged to receive at least a portion of the foot of the patient, wherein the second external member is movable with respect to the first external member;
   at least one joint connecting the first and second external members in a movable manner which allows the patient to walk and bend the ankle; and
   at least one bone securing element configured and arranged to be implanted in the patient's tibia, fibula, or both, the at least one bone securing element including ends configured and arranged to be connected to the first external member, wherein the device is configured and arranged to at least partially unload the ankle joint by transmitting a portion of the weight of the patient from the first external member to the second external member during loading of the ankle.

2. A device according to claim 1, wherein the first external member comprises a cuff.

3. A device according to claim 2, wherein the cuff comprises a front portion, a rear portion, and a connecting mechanism configured and arranged to releasably connect together the front and rear portions.

4. A device according to claim 1, wherein the second external member comprises a shoe including a sole and an upper attached to the sole, the sole including an insole and an outsole.

5. A device according to claim 4, wherein:
   the upper comprises a heal portion configured and arranged to receive the heal of the patient's foot, and a central portion configured and arranged to receive a portion of the patient's foot between the ankle and the toes;
   the upper comprises a heal force transmitting member across the heal portion and an central force transmitting member across the central portion; and
   the heal force transmitting member and the central force transmitting member together being configured and arranged to apply a distracting force to the ankle joint.

6. A device according to claim 4, further comprising:
   at least one foot securing element configured and arranged to be implanted transversely through the patient's foot, the at least one foot securing element including two ends each of which is configured and arranged to be connected to the upper.

7. A device according to claim 6, wherein the at least one foot securing element comprises at least two spaced apart foot securing elements.

8. A device according to claim 6, wherein the at least one foot securing element comprises a pin, a screw, or a wire.

9. A device according to claim 1, wherein the device is not fixed to the bones of the foot or ankle by a bone securing element and the device is configured to at least partially unload the ankle joint without requiring implants in the ankle or foot.

10. A device according to claim 1, further comprising at least one spring arranged at the joint for biasing the joint toward a neutral position.

11. A device according to claim 1, further comprising a second bone securing element configured and arranged to be implanted in one or more of the patient's ankle or foot bones, the second bone securing element including a first portion configured to be implanted in bone and a second portion configured and arranged to be connected to the second external member.

12. A device according to claim 1, further comprising a distraction mechanism configured and arranged to apply a distraction force to the ankle joint.

13. A device according to claim 12, wherein the distraction mechanism is a cable system.

14. A device according to claim 12, wherein the distraction mechanism includes at least one adjustable foot strap.

15. A device according to claim 1, wherein, when the at least one bone securing element is implanted through the patient's tibia, fibula, or both, said first external member is positioned around said portion of the patient's leg between the patient's ankle and the patient's knee, the patient's foot is positioned in the second external member, and said ends of the at least one bone securing element are attached to the first external member, at least a portion of the weight of the patient when standing is transmitted from the patient's leg, through the at least one bone securing element, to the first external member, through the at least one joint, and to the second external member.

16. A device according to claim 1, wherein the at least one bone securing element comprises two bone securing elements oriented perpendicular to each.

17. A device according to claim 1, wherein the at least one bone securing element comprises a pin, a screw, or a wire.

18. A method of treating an ankle of a patient, the method comprising:
providing a device including a first external member configured and arranged to receive a portion of the patient's leg between the patient's ankle and the patient's knee, a second external member configured and arranged to receive at least a portion of the foot of the patient and at least one joint connecting the first and second external members in a movable manner which allows the patient to walk and bend the ankle;
implanting a bone securing element in the patient's tibia, fibula, or both;
positioning the lower leg of the patient in the first external member and securing the first external member to the bone securing element;
positioning the foot of the patient in the second external member; and
transmitting a load from the patient's leg to the ground via the bone securing element, the first external member and the second external member at least partially bypassing the patient's ankle joint.

19. A method according to claim 18, further comprising permitting the ankle to flex at said at least one joint.

20. A method according to claim 18, further comprising generating a distraction force on the ankle joint.

21. A method according to claim 18, wherein the device is not fixed to the bones of the foot or ankle by a bone securing element and the device is configured to at least partially unload the ankle joint without requiring implants in the ankle or foot.

22. A method according to claim 18, wherein the entire weight of the patient is bypassed around the ankle joint by the device.

23. A method according to claim 18, further comprising:
implanting at least one bone implanted member in the patient's foot, before said positioning the foot of the patient in the second external member.

24. A load transferring system for a joint, the system comprising:
a first external brace portion configured and arranged to be attached to at least one bone on one side of said joint by an implantable member;
an entirely external second brace portion configured and arranged to be fixed the other side of the joint without any implantable member; and
a rotatable joint connected to the first portion and the second portion, the rotatable joint configured and arranged to bypass load around the joint.

25. A system according to claim 24, wherein the rotatable joint is configured to bypass around the joint an entire load applied to the joint.

26. A system according to claim 25, wherein in addition to bypassing the load around the joint, the system is configured to apply a distraction force to the joint sufficient to separate the bones of the joint.

27. A system according to claim 24, wherein the first and second external brace portions are configured to accommodate the ankle joint.

28. A system according to claim 27, wherein the second external brace portion is a shoe.

29. A system according to claim 27, wherein the second external brace portion is a shoe insert.

30. A device useful for treatment of a joint of a patient, the device comprising:
a first external member configured and arranged to receive a portion of the patient's joint;
a second external member configured and arranged to receive at least a second portion of the of the patient's joint, wherein the second external member is movable with respect to the first external member;
at least one device joint connecting the first and second external members in a movable manner which allows the joint of the patient to articulate; and
at least one bone securing element configured and arranged to be implanted in a patient's joint bone, the at least one bone securing element including ends configured and arranged to be connected to the first external member, wherein the device is configured and arranged to at least partially unload the joint by transmitting a portion of the joint forces of the patient from the first external member to the second external member during loading of the joint.

31. The device of claim 30, wherein the first external member is attached on a first side of the joint and the second external member is attached on a second side of the joint.

32. The device of claim 30, wherein the joint pivots between the first and second external members.

33. The device of claim 30, further comprising a distraction mechanism configured and arranged to apply a distraction to the joint.

34. The device of claim 33, wherein the distraction member is a cable system.

35. The device of claim 33, wherein the distraction mechanism includes at least one adjustable foot strap.

36. The device of claim 30, further comprising pivoting structure permitting the device to accommodate pivoting of the joint.

37. The device of claim 30, further comprising a pin configured to be inserted in a first bone of the joint.

38. The device of claim 37, further comprising a cuff configured to engage the pin.

39. The device of claim 30, wherein the joint is an ankle joint, and further comprising a pin configured to be inserted in a talus and a cuff configured to engage the pin.

40. The device of claim 30, wherein the joint is an ankle joint, and further comprising a pin configured to be inserted in a tibia and a cuff configured to engage the pin.

41. The device of claim 30, wherein the joint is an ankle joint, and further comprising a first pin configured to be inserted in a talus and a second pin configured to be inserted in a tibia, and a first cuff portion engaging the first pin and a second cuff portion engaging the second pin.

* * * * *